United States Patent
Morero

(10) Patent No.: US 9,199,064 B2
(45) Date of Patent: Dec. 1, 2015

(54) CATHETER GUIDE

(75) Inventor: Massimo Morero, Roncadelle (IT)

(73) Assignee: Invatec S.P.A., Roncadelle (BS) (IT)

( * ) Notice: Subject to any disclaimer, the term of this patent is extended or adjusted under 35 U.S.C. 154(b) by 381 days.

(21) Appl. No.: 13/140,352

(22) PCT Filed: Dec. 18, 2008

(86) PCT No.: PCT/IT2008/000769
§ 371 (c)(1),
(2), (4) Date: Sep. 7, 2011

(87) PCT Pub. No.: WO2010/070685
PCT Pub. Date: Jun. 24, 2010

(65) Prior Publication Data
US 2011/0313402 A1 Dec. 22, 2011

(51) Int. Cl.
*A61M 25/00* (2006.01)
*A61M 25/06* (2006.01)
*A61M 25/01* (2006.01)

(52) U.S. Cl.
CPC ....... *A61M 25/0662* (2013.01); *A61M 25/0041* (2013.01); *A61M 25/001* (2013.01); *A61M 25/007* (2013.01); *A61M 25/008* (2013.01); *A61M 25/0023* (2013.01); *A61M 25/0043* (2013.01); *A61M 25/0053* (2013.01); *A61M 25/0054* (2013.01); *A61M 25/0068* (2013.01); *A61M 2025/0031* (2013.01); *A61M 2025/018* (2013.01)

(58) Field of Classification Search
CPC ..................... A61M 25/0068; A61M 25/0023; A61M 25/0041; A61M 25/0043; A61M 25/0053; A61M 25/0054; A61M 25/007; A61M 25/008; A61M 2025/0031; A61M 25/001; A61M 25/0662; A61M 2025/0018
USPC ......... 604/532, 523, 96.01, 164.01, 264, 524, 604/525, 526, 527, 534
See application file for complete search history.

(56) References Cited

U.S. PATENT DOCUMENTS

| | | | | |
|---|---|---|---|---|
| 4,735,620 A * | 4/1988 | Ruiz | | 604/532 |
| 4,961,731 A * | 10/1990 | Bodicky et al. | | 604/264 |
| 5,088,991 A * | 2/1992 | Weldon | | 604/523 |
| 5,176,661 A * | 1/1993 | Evard et al. | | 604/526 |
| 5,454,795 A * | 10/1995 | Samson | | 604/526 |
| 5,569,219 A * | 10/1996 | Hakki et al. | | 604/524 |
| 2005/0059938 A1* | 3/2005 | Malisch | | 604/265 |
| 2005/0113801 A1* | 5/2005 | Gandras | | 604/523 |
| 2006/0135916 A1* | 6/2006 | Tucker | | 604/264 |
| 2007/0083168 A1 | 4/2007 | Whiting et al. | | |
| 2008/0108975 A1 | 5/2008 | Appling et al. | | |
| 2009/0112153 A1* | 4/2009 | Gregersen et al. | | 604/43 |

FOREIGN PATENT DOCUMENTS

EP 1031328 A1 * 8/2000

* cited by examiner

*Primary Examiner* — Kevin C Sirmons
*Assistant Examiner* — Lauren M Peng

(57) ABSTRACT

This invention concerns a guide catheter comprising a hollow tubular body extending along a main longitudinal axis, said tubular body defining at ] least one internal lumen suitable for receiving at least one medical device, the tubular body further defining at least one proximal opening and one distal opening. The tubular body includes a distal portion preformed in such a way as to take on a curved configuration with regard to the main axis. At least the distal portion of the tubular body has a flattened shape that extends prevalently along a main transversal axis, the curvature of said distal portion being created around said main transversal axis.

16 Claims, 9 Drawing Sheets

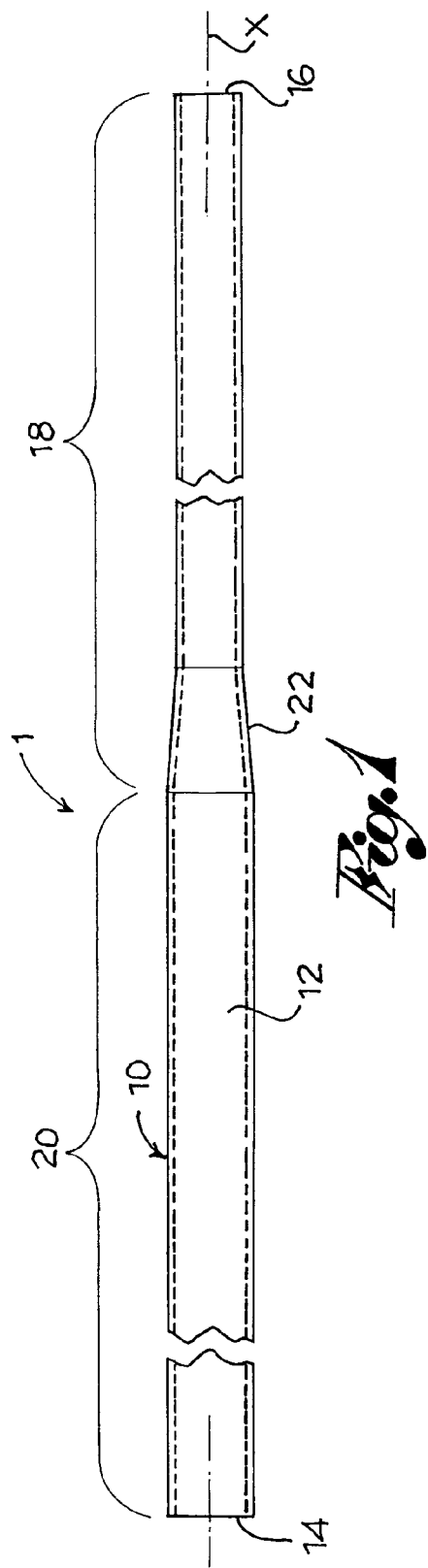
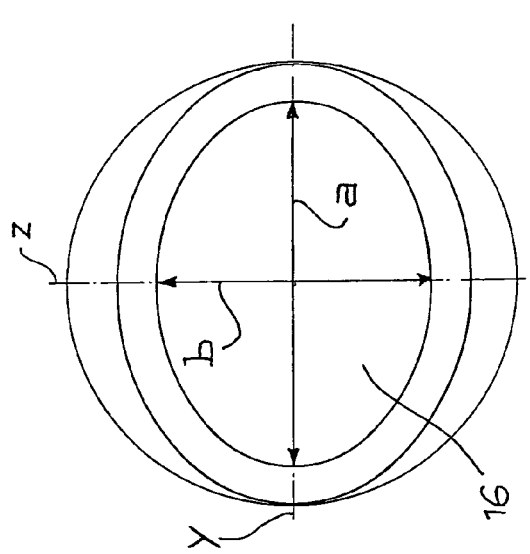
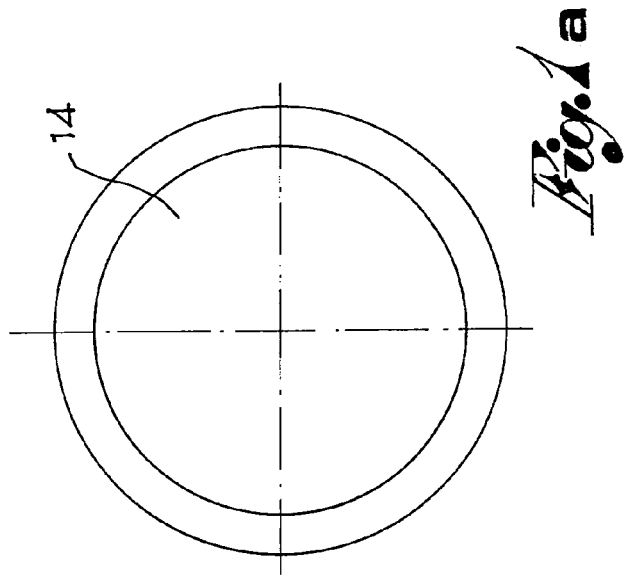

$I_{zz} > I_{yy}$

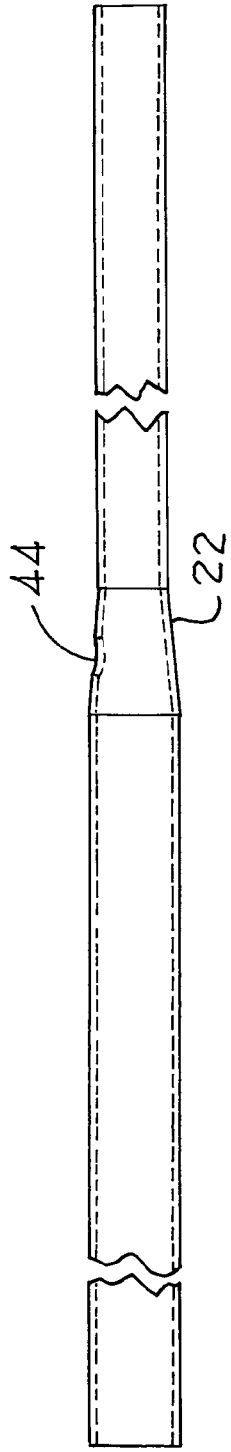
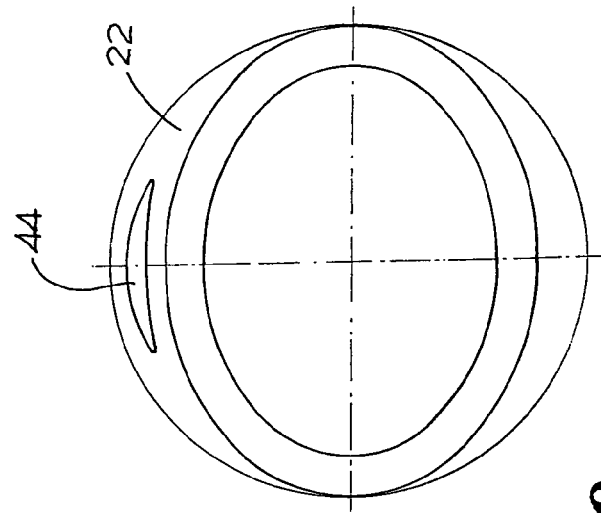
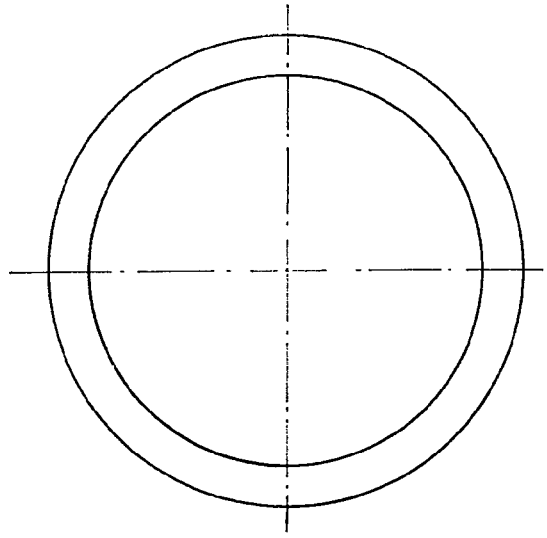
Fig. 9
Fig. 9a
Fig. 9b

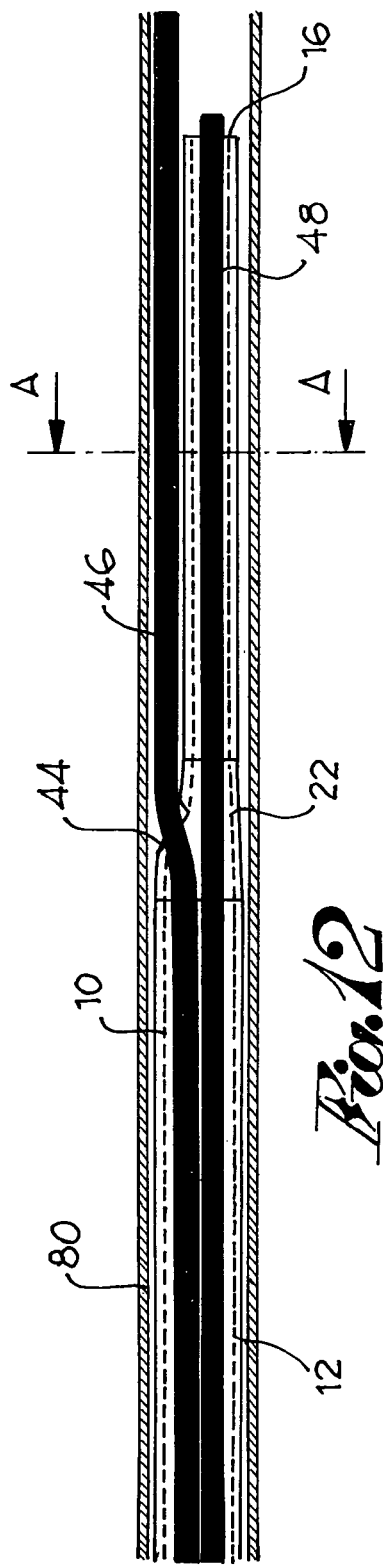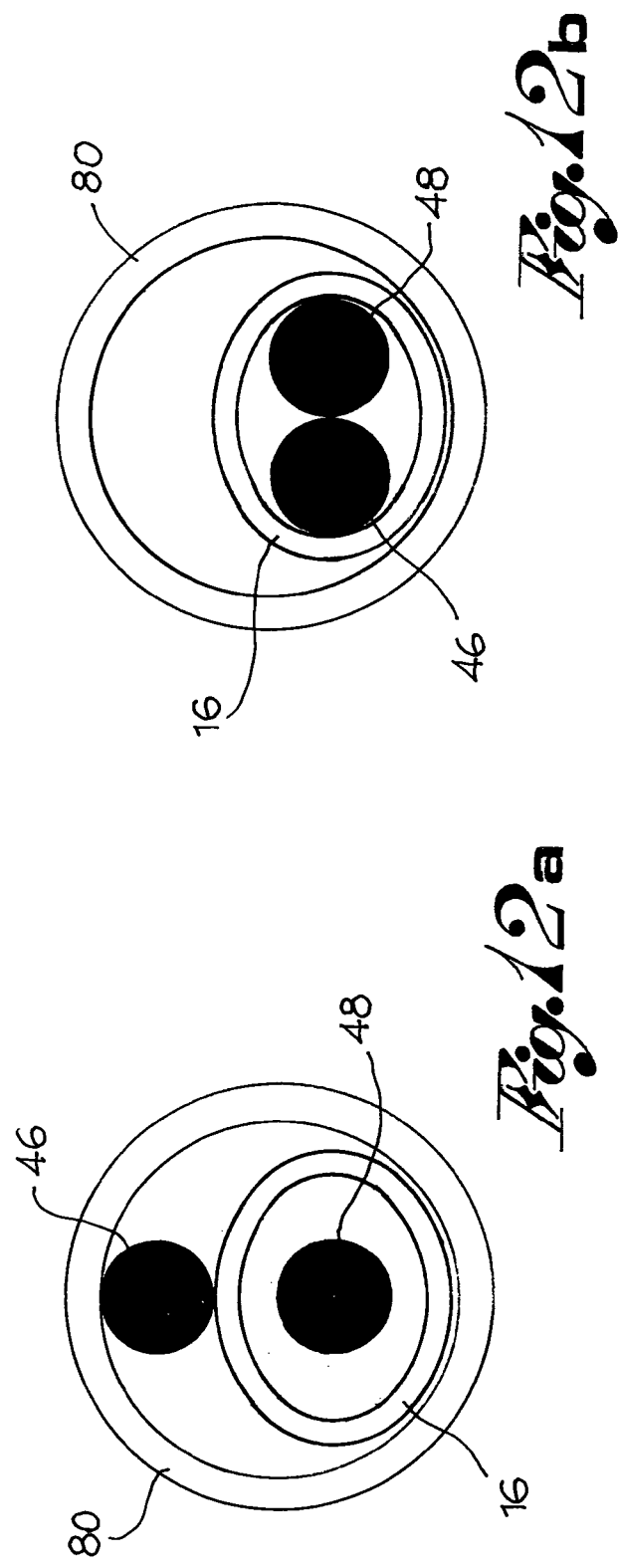

CATHETER GUIDE

This invention regards a guide catheter for performing non invasive operations within a patient's organic cavities, for example in blood vessels. In particular the subject of the present invention is a guide catheter capable of easily directing a guide wire within a blood vessel and, in greater detail, capable of causing this guide wire to pass a bifurcation, for example in the aortic-carotid arch.

Depending on the position of the patient's organic cavity undergoing a non invasive operation as described above, a guide wire may be introduced into a blood vessel with or without the need to employ other means of support, such as for example a micro-catheter. In general, in the case of super-aortic application the guide wire is positioned without the aid of a support means, whereas in the case of a peripheral application below the knee (known as "BTK") the introducer of the guide wire is preferably carried out through use of a micro-catheter. However, especially in cases where the vessel involved is difficult to reach (e.g. a bifurcation in which the secondary vessel or side branch is substantially transversal with regard to the main vessel), the operator (normally a physician) uses the abovementioned support devices which allow directing and positioning of the guide wire in the correct position with view to carrying out the desired operation.

In this case the operator generally uses a guide catheter with the guide wire inside it which passes the bifurcation and positions itself within the side branch. Having reached the bifurcation the guide catheter (with the guide wire positioned within its internal lumen) is turned by the operator in order to line up the tip of the guide catheter with the side branch to be engaged. Subsequently, when alignment has been achieved, the operator drives the guide wire along the internal lumen of the guide catheter, in the direction of and into the transversal side branch.

In order to obtain this result the guide catheter is normally equipped with a tip (which is to say a distal portion) that is curved and highly flexible in comparison with the proximal portion and resistant to the phenomenon known as kinking.

Document U.S. Pat. No. 5,279,596 describes an intravascular catheter with improved resistance to kinking at the tip, even when the latter has a thin and flexible wall. In particular, the catheter described in the abovementioned document includes a proximal portion with an intermediate braid layer to supply high torsional stiffness and a distal portion which carries a helical wire support member embedded therein to provide flexibility and resistance to kinking.

Document U.S. Pat. No. 5,496,294 describes a catheter whose distal portion is made up of an outer tubing liner and an inner stiffener placed coaxially within said liner. The inner stiffener consists of a metal tape of suitable section in the form of a coil, whereas the outer tubing is in a low hardness polymer material. The distal portion of this catheter is highly flexible and resistant to stresses thanks to the reinforcement of the metal coil.

Document US 2008/0172064 describes a system for introducing a plurality of guide wires into a blood vessel, said system comprising a catheter and a first and second guide wire. The catheter has a tapered portion externally in the distal direction and a curved distal portion with sufficient flexibility to slide above the first guide wire. The distal end also has an oval opening of a transversal size sufficient to house the two guide wires in a configuration of reciprocal flanking. Furthermore the catheter, proximally along the curved portion, has a lateral port for passage of the first guide wire, said lateral port being positioned in correspondence to the internal surface of said curved portion.

With view to correct alignment of the tip of a guide catheter with a side branch in correspondence to a bifurcation, the Applicant has noted that the flexibility and resistance to kinking offered by state of the art devices are not sufficient.

In fact, when a state of the art guide catheter is inserted into a blood vessel it is impossible for the operator to know either the effective position of the catheter tip or the direction in which the curved portion of the latter is facing. So having reached the bifurcation zone, with state of the art devices the operator seeks to align the tip of the guide catheter with the opening of the side branch, proceeding by attempts, rotating the device and checking the position of the tip by means, for example, of angiography. This inevitably contributes to increasing both the complexity of the intravascular procedure and its duration.

Moreover, since state of the art devices are not stabilised within the blood vessel, when the tip is positioned in correspondence to the side branch of the bifurcation the guide catheter may move and lose correct alignment, something which inevitably contributes further to increasing duration of the intravascular procedure and risks to the patient's health.

The object of this invention is to realize a guide catheter that can obviate the drawbacks of state of the art devices as mentioned above.

In particular, the Applicant is aware of the need to create a device that can be easily positioned, directed and stabilised within a blood vessel in such a way that the operator can direct a guide wire into the side branch of a bifurcation of said vessel with a simple, fast and safe procedure.

The Applicant has found that this objective may be advantageously achieved by creating a guide catheter with at least the distal portion preformed in such a way as to take on a curved configuration with regard to the longitudinal axis of the guide catheter itself, in which said distal portion has a flattened transversal section. In fact this construction of the distal portion of the guide catheter, as will be seen below, allows the operator to correctly position the distal portion (which is to say the tip of the guide catheter) with regard to the opening of the side branch and therefore engage the latter in a simple, rapid and safe way.

So one object of this invention is a guide catheter including a hollow tubular body extending along a main longitudinal axis, said tubular body defining at least one internal lumen suitable for receiving at least one medical device, the tubular body further defining at least one proximal opening and a distal opening, said tubular body including a distal portion preformed in such a way as to take on a curved configuration with regard to said main axis, in which at least said distal portion has a flattened shape which extends prevalently along a main transversal axis, the curvature of said distal portion being created around said main transversal axis.

A further object of this invention is a kit comprising:
- an introducer sheath defining an internal lumen which extends between a proximal and a distal opening;
- a guide catheter as described above, said guide catheter being suitable for insertion and sliding within the internal lumen of said sheath, and
- a guide wire emerging from the lateral opening of the guide catheter and extending parallel to and outside the distal portion of the guide catheter, in which the diameter simultaneously occupied by the distal part of the guide catheter and the guide wire is such as to be contained in the internal lumen of the introducer sheath.

Further characteristics and advantages of the guide catheter according to the invention will be apparent from the description below of preferred embodiments, given by way of example and not limitative, with reference to the annexed drawings, in which:

FIG. 1 illustrates a longitudinal section view of a guide catheter device in accordance with the invention;

FIG. 1a is a view of the extremity of the proximal portion of the guide catheter in FIG. 1;

FIG. 1b is a view of the extremity of the distal portion of the guide catheter in FIG. 1;

FIG. 9 illustrates a longitudinal section view of a variant of implementation with lateral opening of the guide catheter in accordance with this invention;

FIG. 9a is a view of the extremity of the proximal portion of the guide catheter in FIG. 9;

FIG. 9b is a view of the extremity of the distal portion of the guide catheter in FIG. 9;

FIG. 12 is a longitudinal section view of the guide catheter, in accordance with the embodiment with lateral opening in FIG. 9, inserted in an introducer sheath and carrying two guide wires; and FIGS. 12a and 12b are two transversal sections along the line A-A of the guide catheter in FIG. 12, at two different moments of the intravascular procedure.

Figure 2A:
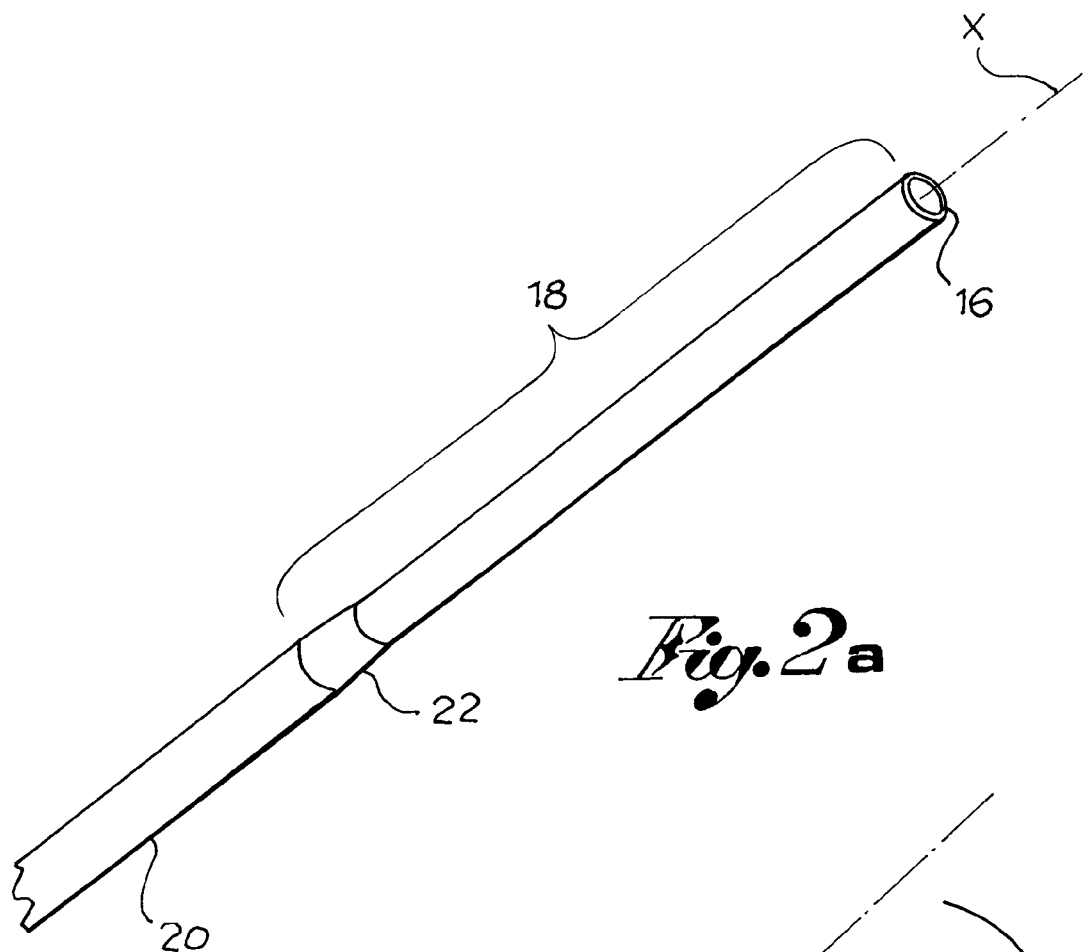
FIG. 2a is a perspective view of the distal portion, in rectilinear configuration, of the guide catheter in accordance with the invention.

In accordance with one embodiment of the invention, shown in FIG. 1, guide catheter 1 comprises a hollow tubular body 10 which extends along a main longitudinal axis X and defines at least one internal lumen 12 suitable for receiving at least one medical device. Preferably, said medical device is at least one guide wire.

Tubular body 10 extends between at least one proximal opening 14 and a distal opening 16.

Guide catheter 1 has a proximal portion 20, substantially rectilinear, and a distal portion 18 defining the tip (which is to say the terminal part) of the hollow tubular body 10.

Figure 2B:
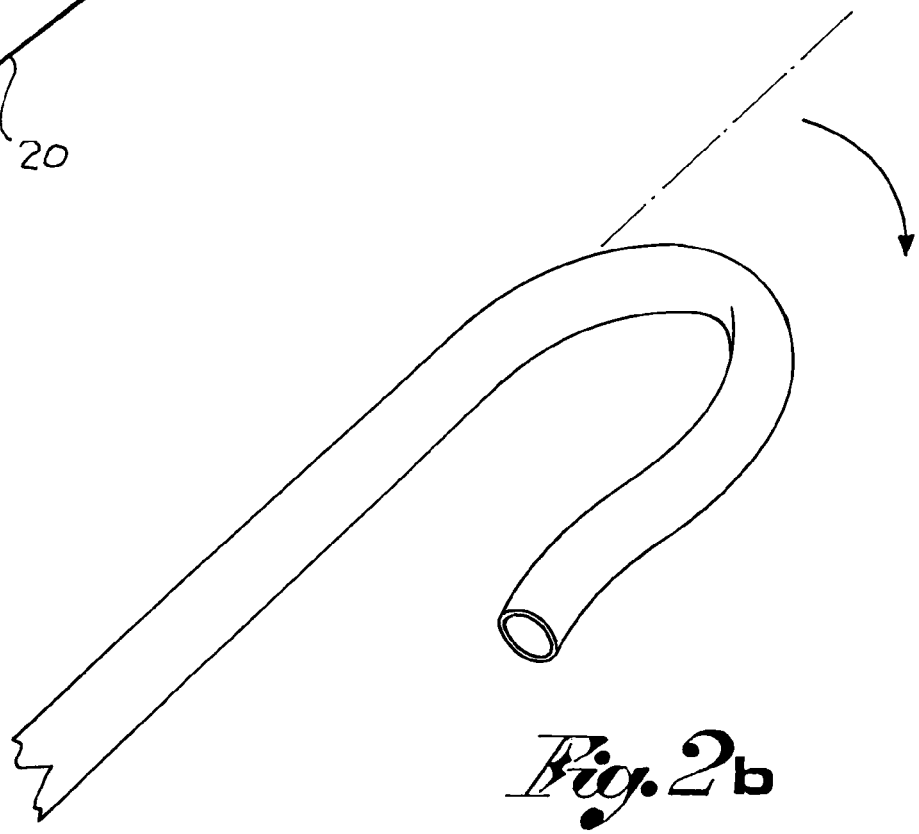
FIG. 2b is a perspective view of the distal portion, in curved configuration, of the guide catheter in accordance with the invention.

Said distal portion 18 is preformed (see in particular FIG. 3) in such a way as to take on a curved configuration with regard to said main axis X with view to intercepting the bifurcation of a blood vessel (i.e. the side branch setting out from a main vessel). Preferably the distal portion 18 of guide catheter 1 recalls memory in passing from a rectilinear configuration, (illustrated for example in FIG. 2a) when it contains a rigid guide element (e.g. a guide wire), to a curved configuration (illustrated for example in FIG. 2b), when said guide element is unwired or when a flexible portion of said guide element is brought into correspondence to the distal portion of the guide catheter.

In accordance with an advantageous embodiment the distal portion 18, when in rectilinear configuration, has its longitudinal axis coinciding with the main longitudinal axis of the proximal portion.

In conformity with the embodiment illustrated in FIG. 1, when distal portion 18 is in the curved configuration (FIG. 2b and FIG. 3), said distal portion has a main U-curve or hook 50. So when distal portion 18 is in the curved configuration, guide catheter 1 takes on an overall J-shape.

Preferably main curvature 50 has an average radius R between 3 mm and 9 mm, and even more preferably between 4 mm and 6 mm. Average radius R is measured—from curvature centre O in FIG. 3—in correspondence to the average axis of curvature portion 50, said axis (illustrated with a dotted line in FIG. 3) coinciding with longitudinal axis X when the guide catheter is in the rectilinear configuration.

Preferably, the terminal part of distal portion 18, which contains distal opening 16, has a second curvature or contra-curvature 52) on the part opposite the main curvature 50 in such a way as to facilitate engagement with a side branch of the main vessel in which the guide catheter is inserted.

So when the distal portion 18 of guide catheter 1 is free to bend, it substantially takes on an S-shape, the second curved portion of the S being less accentuated than the first.

Figure 3:
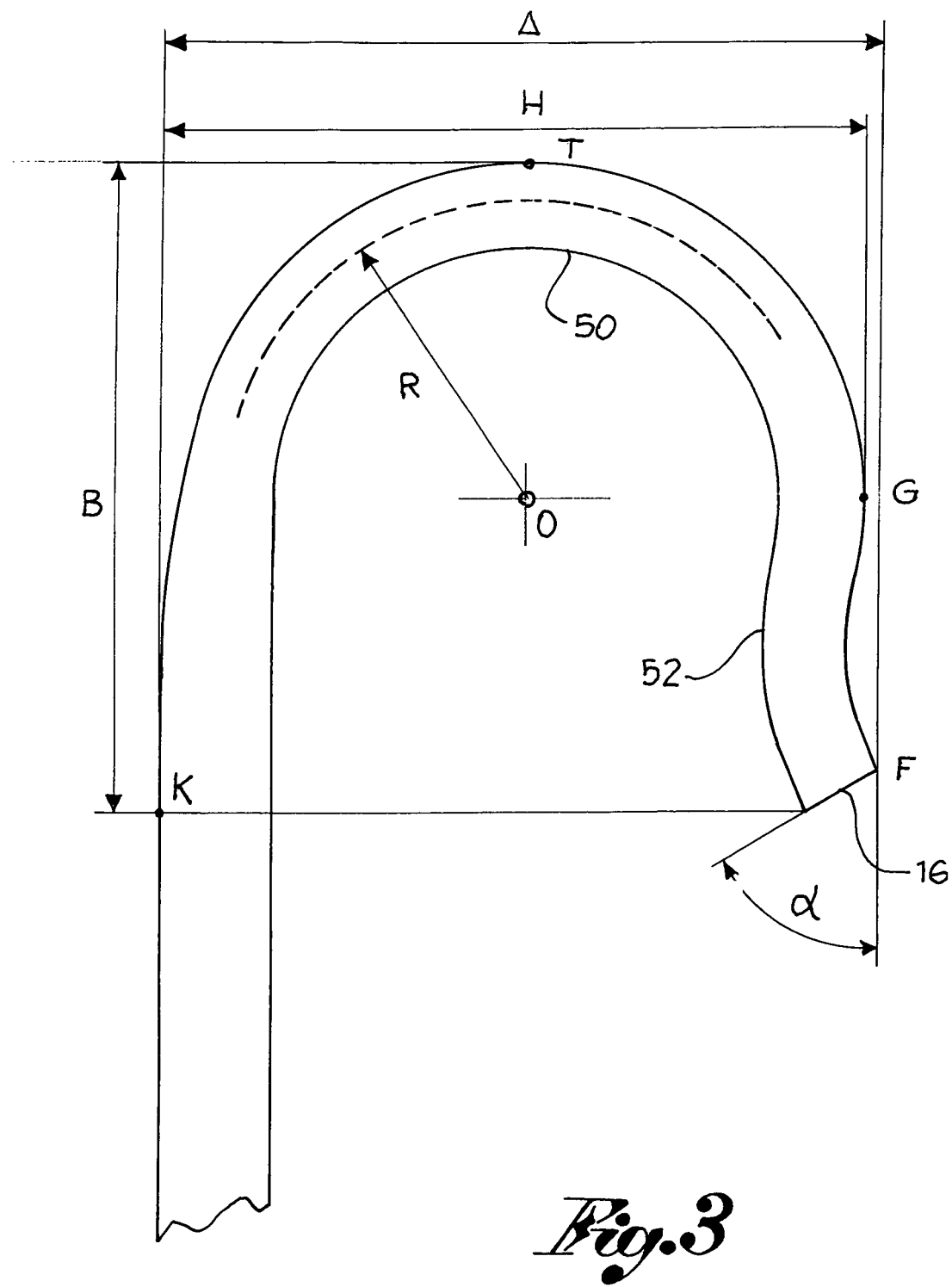
FIG. 3 illustrates an elevation view of the distal portion, in the curved configuration, of the guide catheter in accordance with the invention.

With reference to FIG. 3, where A indicates maximum width of the abovementioned "S" configuration, said width being measured from point K of tangency of main curvature 50 with the rectilinear part of the guide catheter to extremity F of distal opening 16, said width therefore including both the width of main curvature 50 and contra-curvature 52). A is preferably between 13 mm and 19 mm.

With reference to FIG. 3, where H indicates maximum width of main curvature 50 (said width being measured from tangency point K of main curvature 50 with the rectilinear part of the guide catheter to the starting point—flex point G—of contra-curvature 52), H being preferably between 10 mm and 14 mm.

With reference to FIG. 3, B indicates the maximum extension (length) of the abovementioned "S" configuration (said extension being measured from tangency point K of main curvature 50 with the rectilinear part of the guide catheter to the maximum point T of main curvature 50). B is preferably between 10 mm and 16 mm.

Preferably, distal opening 16 of guide catheter 1 is created with a transversal cut in hollow tubular body 10 of said guide catheter. This transversal cut is made in accordance with inclination angle α (measured with regard to an axis substantially parallel to longitudinal axis X of guide catheter 1), preferably between 20° e 70° and more preferably between 40° and 60°.

In accordance with the embodiment of this invention illustrated in FIG. 1, proximal portion 20 of guide catheter 1 has a substantially circular extremity section (see for example FIG. 1a).

In accordance with this invention, at least distal portion 18 of guide catheter 1 has a crushed or flattened shape which extends prevalently along a main transversal axis Y (see for example FIG. 1b).

In other words, at least distal portion 18 of guide catheter 1 does not extend in an axial-symmetrical way around main longitudinal axis X (considering the distal portion in rectilinear configuration) but has a favoured or prevalent extension in the transversal direction Y (direction Y being directed transversally with regard to longitudinal direction X and set in a plane substantially perpendicular to the plane of FIG. 1).

Preferably, the shape of distal portion 18 (said shape being obtained by means of a transversal section of distal portion 18 in accordance with a plane perpendicular to axis X) transversally defines a greater diameter "a" (along axis Y) and a lesser diameter "b" (along axis Z): see in particular FIG. 1b. In this description the expression "crushed or flattened shape" of distal portion 18 means that greater diameter "a" of said distal portion is at least 20% more than lesser diameter "b" of said distal portion.

Even more preferably, distal portion 18 of guide catheter 1 is of a substantially elliptical or oval section.

In accordance with a further embodiment (not illustrated) the guide catheter has a crushed or flattened shape along the entire longitudinal extension of the catheter itself.

Figures 4, 4A:
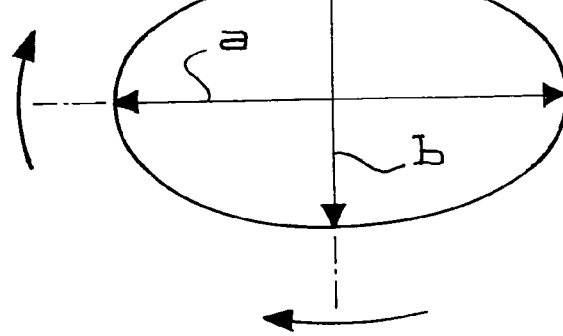
FIG. 4 illustrates an elevation view of the whole guide catheter in accordance with the invention, in the curved configuration.
FIG. 4a is a diagram of the inertia moments of the guide catheter with regard to its main transversal axes Y and Z.

In conformity with the invention, the curvature of the distal portion (meaning both main curvature 50 and contra-curvature 52) is created around said transversal axis Y (see for example FIG. 4) which identifies the prevalent extension (greater diameter "a") of the transversal section of said distal portion 18. In other words, the flattening (in transversal section) along axis Z of distal portion 18 of guide catheter 1 in this invention means that the abovementioned distal portion can bend in correspondence to its surface with greater radius of curvature. So thanks to the abovementioned flattened configuration the transversal section of said distal portion 18 can turn with greater facility around axis Y. In fact, thicknesses being equal, the distal portion with greater radius of curvature offers greater flexibility, which is to say less resistance to curvature (or rotation) in comparison with the distal portion with lesser radius of curvature, as shown in FIG. 4a.

In accordance with a particularly advantageous embodiment, distal portion 18 is tapered towards distal opening 16.

Preferably, the tapering involves two opposite lateral surfaces, symmetrical with regard to transversal axis Y. In other words, the distal portion is flattened solely with regard to a transversal axis (axis Z), coinciding with lesser diameter "b". In yet other words, the greater diameter "a" of the distal portion coincides with the diameter of proximal portion 20 (which constitutes the longer part of the guide catheter with a substantially circular section), while lesser diameter "b" of the distal portion is smaller than the diameter of proximal portion 20.

Figure 5:
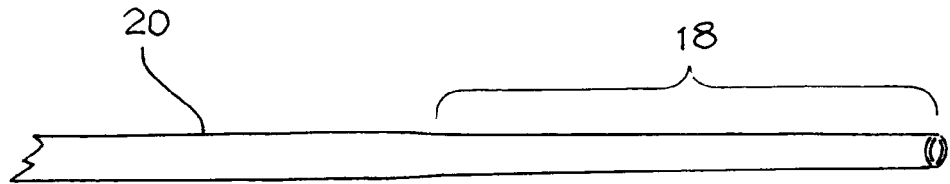
FIG. 5 is a perspective view of the distal portion, according to a further embodiment of the guide catheter in accordance with this invention.

In accordance with one embodiment of the guide catheter according to the invention illustrated in FIG. 5, the tapering is substantially continual along the whole of distal portion 18, which is to say it concerns the distal portion axially along its entire longitudinal extension.

In accordance with one embodiment of the guide catheter according to the invention illustrated in FIG. 1, tapering is localised in a transition portion 22 which connects distal portion 18 to proximal portion 20 of hollow tubular body 10.

In accordance with this invention, distal portion 18 of the guide catheter (see in particular FIG. 6) includes a support element 24 (coil). Preferably this support element is of a filiform type. Alternatively it may be ribbon-like. This construction is especially advantageous inasmuch as it permits countering the kinking phenomenon of the tip during the guide catheter's movement within a blood vessel, even when the tip is in a particularly flexible material and with a very thin wall.

Figure 6:
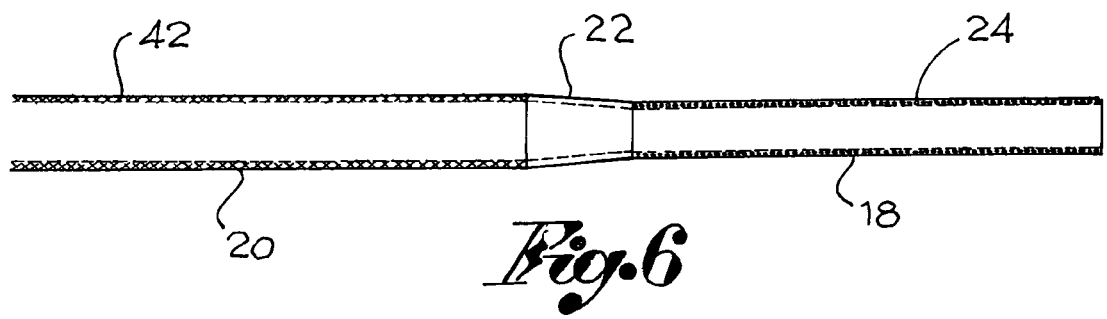
FIG. 6 is a longitudinal section view of the distal portion, according to one embodiment of the guide catheter in accordance with this invention.

In accordance with the embodiment illustrated in FIG. 6, the proximal portion 20 of the guide catheter in accordance with this invention includes an internal support layer created with a braided wire 42 capable of supplying the guide catheter with considerable torsional stiffness as it proceeds within a blood vessel. This characteristic of torsional stiffness is advantageous inasmuch as it contributes to improving the "torqueability" of the whole device, meaning the operator's ability to direct the distal portion of the guide catheter by acting directly on its proximal extremity.

In accordance with the embodiment illustrated in FIG. 6, transition portion 22 has no internal support element. Alternatively, transition portion 22 has at least one internal support element that ensures appropriate mechanical resistance to the transition portion itself, especially when both the distal portion 18 and the proximal portion 20 are equipped with respective support structures.

Although FIG. 6 simultaneously represents the embodiment where distal portion 18 of the guide catheter includes a spiral support element 24, the embodiment where proximal portion 20 of the guide catheter includes an internal layer of support created with braided wire 42 and the embodiment where transition portion 22 has no internal support element, the coexistence of these embodiments in the same device does not present any constructional limitation: the abovementioned embodiments may be used distinctly or in any combination thereof.

In accordance with a further embodiment of the invention, the hollow tubular body 10 has variable flexibility in an axial direction. This flexibility preferably increases in the distal direction.

Hollow tubular body 10 may be provided with variable flexibility in an axial direction (meaning along its longitudinal development) providing said hollow tubular body 10 with axially adjacent portions created in different materials with differing flexibility.

Figure 7:
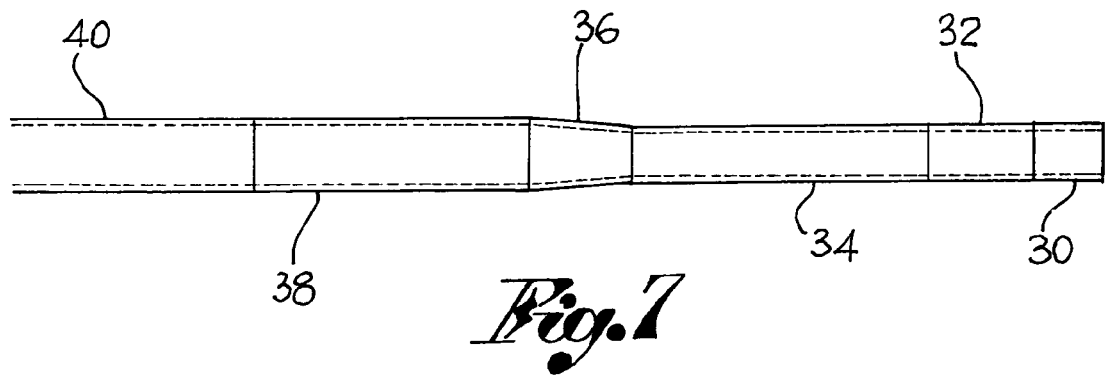
FIG. 7 is a longitudinal section view of the distal portion, according to a further embodiment of the guide catheter in accordance with this invention.

For example, with reference to FIG. 7 and setting out from the distal extremity of the hollow tubular body, the latter may be provided with a first portion 30 in polymeric material (e.g. PEBA) with Shore D hardness equal to 35. The second portion 32 may be made for example in a polymeric material (such as PEBA) with Shore D hardness equal to 55. The third portion, the main part of the distal portion, may be made in a polymeric material (e.g. PEBA) with Shore D hardness equal to 35. The fourth portion 36, which corresponds to the tapered transition portion, may be made in a polymeric material (e.g. PEBA) with Shore D hardness equal to 55. The fifth portion may be made for example in a polymeric material (e.g. PEBA) with Shore D hardness equal to 63. The sixth portion 40, which constitutes the greater part of the proximal portion of the hollow tubular body, may be made for example in a polymeric material such as Polyamide 12 (PA 12) or PEBA with Shore D hardness equal to 72.

Figure 8:
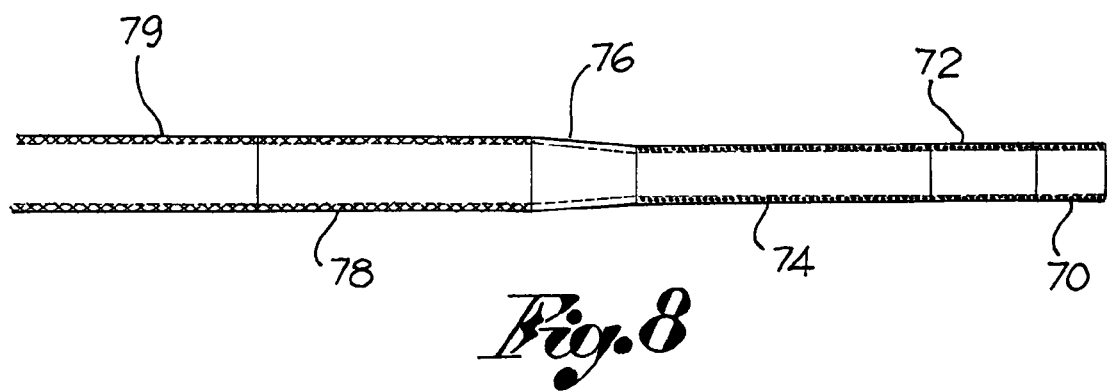
FIG. 8 is a longitudinal section view of the distal portion, according to a further embodiment of the guide catheter in accordance with this invention.
Figure 10A:
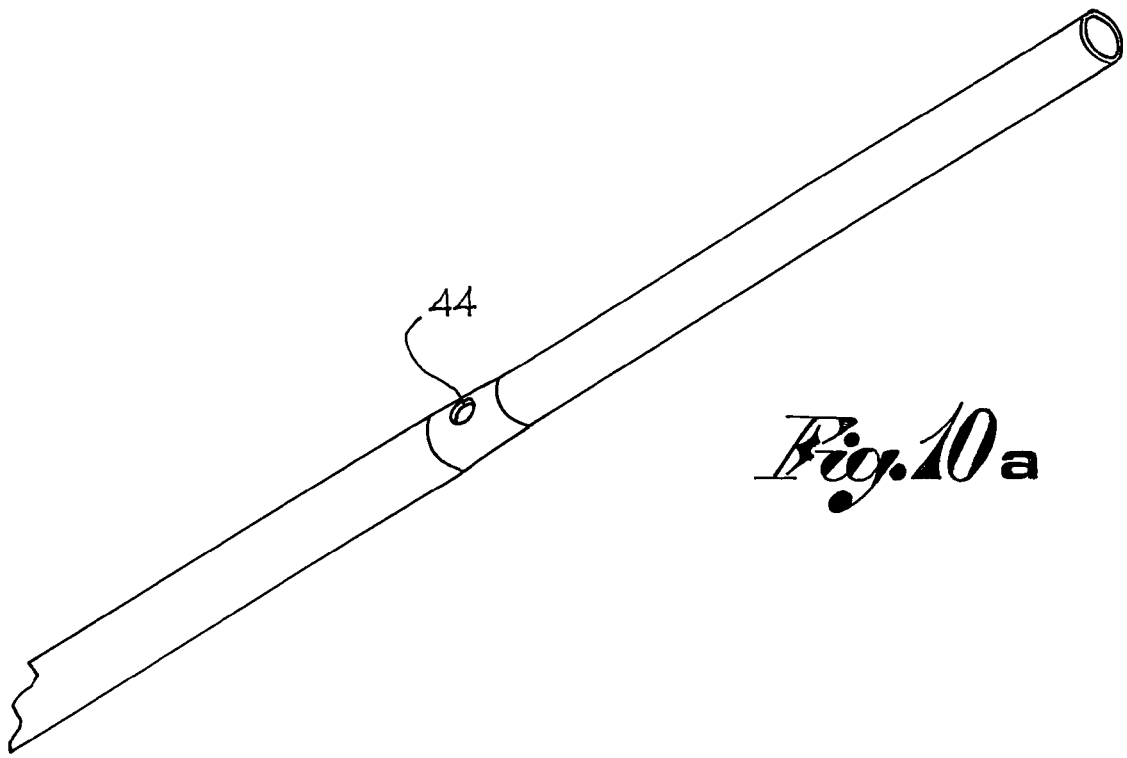
FIG. 10a is a perspective view of the distal portion, in rectilinear configuration, of the guide catheter in accordance with the embodiment with lateral opening in FIG. 9.
Figure 10B:
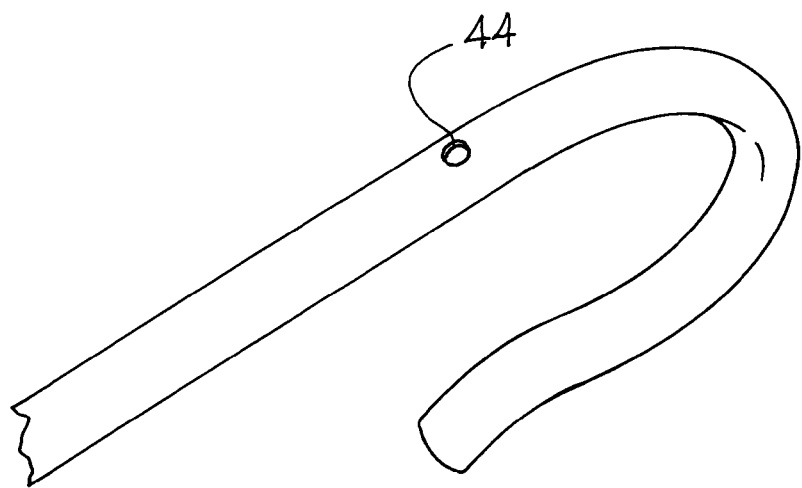
FIG. 10b is a perspective view of the distal portion, in curved configuration, of the guide catheter in accordance with the embodiment with lateral opening in FIG. 9.

In accordance with a further embodiment illustrated in FIG. 8, hollow tubular body 10 has a mixed construction obtained through the use of internal support layers (braid in the proximal and coil in the distal zones) incorporated within different materials with different flexibilities, in particular with flexibility increasing in the distal direction.

For example, setting out from the distal extremity of hollow tubular body 10 in FIG. 8, the latter has a first portion 70 comprising a metal coil (preferably in stainless steel or in a chromium and cobalt alloy) incorporated in a layer made, for example, of a polymeric material (e.g. PEBA) with Shore D hardness equal to 35. The second portion 72 comprises a metal coil incorporated in a layer of, for example, polymeric material (e.g. PEBA) with Shore D hardness equal to 55. The third portion 74 comprises a metal coil incorporated in a layer of, for example, polymeric material (e.g. PEBA) with Shore D hardness equal to 35. The fourth portion 76, which corresponds to the tapered transition portion, is in polymeric material (e.g. PEBA) with Shore D hardness equal to 55, said fourth portion being without any support layer. The fifth portion 78 comprises an internal braid element incorporated in a layer of, for example, polymeric material (e.g. PEBA) with Shore D hardness equal to 63. The sixth portion 79, which constitutes the greater part of the proximal portion of the hollow tubular body, comprises a braid element incorporated in a polymeric material such as Polyamide 12 (PA 12) or PEBA with Shore D hardness equal to 72.

In accordance with this invention, thanks to the flattened transversal section of distal portion 18 of the guide catheter, the procedure of aligning the tip of the guide catheter with a side branch in correspondence to a bifurcation is considerably simplified for the operator (above all when said side branch extends in a direction that is substantially transversal to the direction of the main vessel from which said side branch diverts).

As mentioned above, the guide catheter in accordance with this invention is first fitted on the proximal part of a guide wire already positioned within a blood vessel and subsequently proceeds, running on this guide wire, until it reaches the zone in question (e.g. a bifurcation). The proximal portion of the guide wire is generally more rigid than its distal portion. This stiffness of the proximal part of the guide wire means that the preformed flexible tip of the guide catheter can be straightened and the guide catheter can easily proceed to the zone in question. When the guide wire is at least partially retracted by the operator, which is to say when the distal portion of the guide wire (generally more flexible than the proximal portion) is within distal portion 18 of the guide catheter, the flexibility of said distal portion 18 allows the preformed tip of the guide catheter to return to its original curved form (preformed configuration). In accordance with this invention the flattened shape of distal portion 18 of the guide catheter is especially advantageous in this specific phase of the intravascular procedure inasmuch as it facilitates both bending and directing of the guide catheter tip as referred to above.

In fact, considering for simplicity's sake the embodiment illustrated in FIG. 4a (where the distal portion has a substantially elliptical transversal section), as already pointed out, said elliptical section involves the formation of two main axes, Y and Z, at right angles, and two corresponding diameters, a and b.

Thanks to the flattened shape (elliptical in FIG. 4a) of the distal portion, the inertia moment "Iyy" with regard to axis Y is different from the inertia moment "Izz" with regard to axis Z. In particular, the inertia moment around lesser axis Z is greater with regard to the inertia moment around greater axis Y. So applied force being equal, since the elliptical tip can bend (turn) with greater facility around the greater axis Y, this will be precisely the curvature direction followed by the distal portion of the guide catheter.

In conclusion, the elliptical tip has two preferential curvature directions (from one side or the other around greater axis Y of the elliptical section) and if the guide catheter is correctly designed, meaning that if the distal portion is preformed around one of these two directions, one of them coincides with the effective curvature direction of the distal portion. In other words, the flattened transversal section of the distal portion of the guide catheter according to the invention creates two preferential inertia directions: maximum flexibility corresponds to one direction and maximum stiffness to the other.

In conformity with this invention the elliptical section of distal portion 18 of the guide catheter permits the latter to position itself within the blood vessel in such a way that the tip of the guide catheter is correctly aligned and stably positioned at the mouth of the side branch of the bifurcation.

Where contrarily the tip of the guide catheter has a perfectly circular transversal section, the moment of inertia will be identical along both transversal axes. So in this configuration there is no preferential curvature, with the disadvantage that, in correspondence to the bifurcation, the tip of the guide catheter could bend in any direction without any possibility of control on the operator's part.

With particular regard to the tip directing phase, with view to positioning the guide catheter correctly, during the intravascular procedure the operator intervenes of the proximal part of the guide catheter, setting up rotation along main longitudinal axis X. Thanks to the flattened section (along transversal direction Z in the figures) of the distal section of the guide catheter according to the invention, the rotation applied by the operator meets with greater resistance in the direction of greater stiffness (i.e. in direction Y), a resistance which translates into a greater reaction (or response) of the guide catheter precisely in that direction (i.e. direction Y). Since "torqueability" indicates the catheter's capacity to correctly and rapidly transmit the rotation applied by the operator in the proximal zone to the distal zone, the result is that the flattened section of the tip of the guide catheter in this invention improves the "torqueability" of the whole device.

As pointed out above, if the catheter tip had a circular section, the transversal axes of said section would both have the same moment of inertia, so there would be no direction of greater stiffness. Therefore the circular section would not contribute to improving transmission of rotation from the proximal to the distal zone of the guide catheter and there would be no improvement in the torqueability of the device.

In conclusion, therefore, the flattened shape of the distal portion of the guide catheter in accordance with this invention translates into greater flexibility of the tip and greater ease of device control and direction, characteristics that are particularly desirable, above all when the side branch of a bifurcation is to be engaged.

As regards the procedure of directing the guide catheter in accordance with the invention, once it is positioned in correspondence to the bifurcation the operator need only verify, for example by angiography, that the catheter is positioned with the crushed (or flattened) surface of its distal portion facing the side branch. In this way when distal portion 18 resumes its curved conformation (following at least partial retraction of the guide wire set within the guide catheter), the tip of the guide catheter will advantageously be directed towards the opening of said side branch.

Furthermore, thanks to the flattened shape of distal portion 18 of the guide catheter in accordance with the invention, there is less risk of accidental rotation or other movement of the guide catheter that might cause loss of correct position of alignment with the bifurcation.

The embodiment of this invention in which the flattened section is envisaged along the whole extent of the guide catheter (and not only limited to the latter's distal portion), is particularly advantageous inasmuch as the operator can easily check the correct angular positioning of the device within the blood vessel simply by visual observation of the proximal portion of the guide catheter, which is external to the patient's body. In fact in this case the spatial orientation of the proximal section of the catheter, identifiable since it is visible to the operator (said proximal section being external to the patient's body), will coincide with the spatial orientation of the distal section of the guide catheter in correspondence to the bifurcation zone.

In accordance with a further embodiment of this invention shown in FIGS. 9-12, in correspondence to distal portion 18, preferably in the tapered transition portion 22, there is at least one lateral opening 44 for the passage of at least one guide wire 46 (as illustrated for example in FIG. 12).

Advantageously this lateral opening 44 is located on external surface 90, set from the opposite side with regard to the curvature direction of distal portion 18. The centre of average radius R of main curvature 50 being indicated by O, lateral opening 44 (in particular the proximal mouth of said opening) is positioned proximally with regard to said centre O, preferably at distance D, between 1 mm and 20 mm.

In accordance with such a embodiment, the guide catheter in accordance with this invention advantageously allows correct and simultaneous positioning of more than one medical device, as further illustrated in detail below.

Generally a guide catheter is made to run on a guide wire previously positioned within a blood vessel. Since the guide catheter must be inserted into the patient's body, the distal part of the guide catheter is fitted to the guide wire already positioned in the blood vessel. In particular the proximal part of the guide wire is inserted into the lumen of the tubular body of the guide catheter itself. The guide catheter (with the guide wire positioned in its internal lumen) is then inserted into an introducer sheath or introducer 80 (see FIG. 12), said introducer having an internal diameter compatible with the external diameter of the guide catheter. The introducer is typically of such a length as to pass the iliac bifurcation, known as carrefour.

Figure 11:
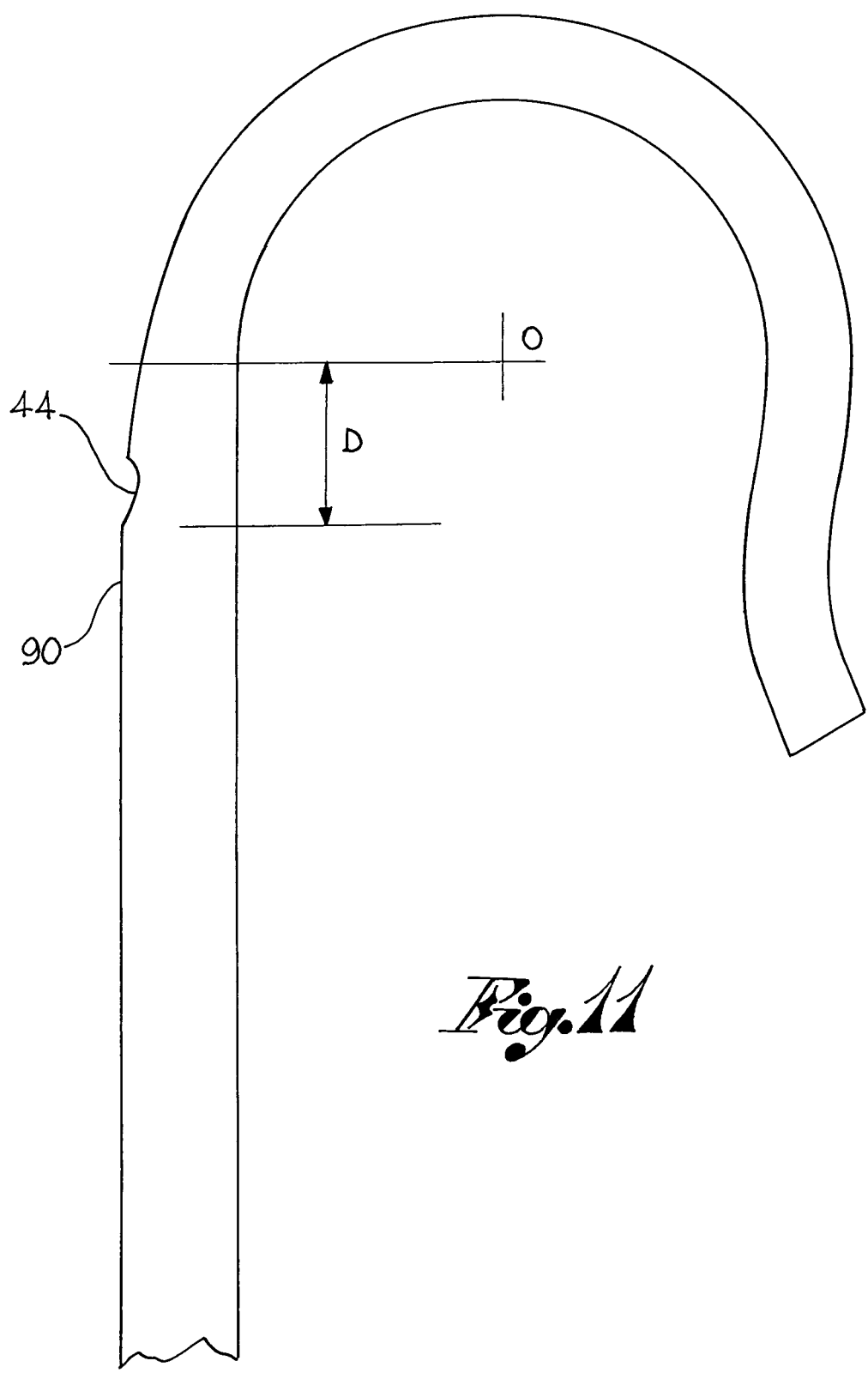
FIG. 11 illustrates an elevation view of the distal portion of the guide catheter, in the curved configuration, in accordance with the embodiment with lateral opening in FIG. 9.

In accordance with the abovementioned further embodiment shown in FIG. 11, where the external surface of the guide catheter has a lateral opening 44, the guide catheter is fitted on a first guide wire 46 (generally rigid and already positioned in the blood vessel) through lateral opening 44. In particular, guide wire 46 is inserted, through lateral opening 44, into the internal lumen 12 of hollow tubular body 10 in such a way that a portion of guide wire 46 (in particular its distal part) projects from lateral opening 44 and runs parallel to distal portion 18 of the guide catheter. So when the guide catheter reaches the bifurcation zone, the first guide wire 46, which projects out of lateral opening 44, lies on the internal wall of the main vessel and carries out the function of stabilising the guide catheter in the desired position.

A second guide wire 48 (generally more flexible than first guide wire 46) is inserted into the internal lumen 12 of hollow tubular body 10 of the guide catheter and projects from distal opening 16 of the guide catheter. Guide wire 48 may be inserted into the guide catheter by means of proximal opening 14 of the catheter or, when guide wire 48 is already positioned within the patient's body, the guide catheter is fitted to guide wire 48 through distal opening 16. This second guide wire 48, which initially has the function of straightening the curved distal portion 18 of the guide catheter to facilitate the operation of insertion and advancement of the catheter in the patient's cavity (e.g. a blood vessel), is the guide wire which will be subsequently pushed by the operator into the side branch of the bifurcation.

Favourably, the guide catheter in accordance with this further embodiment may be inserted into introducer sheath 80 more or less simultaneously with first guide wire 46 which projects from lateral opening 44 and runs parallel to distal portion 18 of the guide catheter. In the case of the distal portion of the guide catheter having a circular section, even of small diameter (rather than flattened, for example elliptical, as in this invention), the operator would not be able to make the two devices (guide catheter 1 and first guide wire 46) proceed simultaneously within introducer sheath 80. The flattened tip in the invention, on the contrary, permits this simultaneous insertion. In fact guide catheter 1 can be set on introducer sheath 80 with the flattened part of the distal portion 18 and the overall external diameter (given by lesser diameter b along lesser axis Z of the tapered portion and by the diameter of the first guide wire 46) is compatible with the internal diameter of the lumen of introducer sheath 80 (see for example FIG. 12a).

This further embodiment, having distal portion 18 with flattened transversal section and with lateral opening 44, with equal overall external diameter, means that first guide wire 46 can be withdrawn (and made to enter opening 44) and that the two guide wires 46 and 48 can be made to advance simultaneously within the guide catheter, as illustrated in the transversal section of FIG. 12b.

Moreover, where the embodiment of this invention envisages a tapering 22 of distal portion 18, it is particularly advantageous to provide said tapered portion 22 with lateral opening 44 inasmuch as said lateral opening is not subjected to stresses by guide wire 46. In fact, in this configuration, guide wire 46 can emerge from lateral opening 44 without curving brusquely and can be set gently, parallel to distal portion 18 of the guide catheter.

To meet contingent needs a man skilled in the art could, with regard to the guide catheter described above, modify and adapt elements, or replace them with others that are functionally equivalent, without going beyond the scope of protection as defined by the following claims. Each of the characteristics described as belonging to a possible embodiment may be implemented independently of the other forms of implementation described.

The invention claimed is:

1. A guide catheter kit comprising:
    a guide catheter comprising,
        a hollow tubular body extending along a longitudinal axis, said tubular body defining at least one internal lumen suitable for receiving at least one medical device, the tubular body further defining a proximal opening, a lateral opening for receiving a guidewire there through and a distal opening, said tubular body including a distal portion preformed in such a way as to assume a curved configuration with regard to said longitudinal axis, wherein at least said distal portion has a flattened shape which extends prevalently along a transverse axis, wherein the curvature of said distal portion is created around said transverse axis, and wherein said lateral opening is created through an external surface on an opposite side of the tubular body with regard to a direction of the curvature of said distal portion;
    an introducer sheath defining an internal lumen that extends between a proximal opening and a distal opening, wherein said guide catheter is sized to be inserted and to run within the internal lumen of said sheath; and a guide wire emerging from the lateral opening of the guide catheter and extending parallel and external to the distal portion of the guide catheter when the distal portion of the guide catheter and the guide wire are simultaneously contained in the internal lumen of the introducer sheath.

2. The guide catheter kit in accordance with claim 1, wherein the flattened shape of the distal portion of the hollow tubular body transversally defines a greater diameter (a) and a lesser diameter (b).

3. The guide catheter kit in accordance with claim 2, wherein the distal portion of the hollow tubular body has a cross-section that is substantially elliptical.

4. The guide catheter kit in accordance with claim 1, wherein the distal portion of the hollow tubular body includes a tapering towards the distal opening.

5. The guide catheter kit in accordance with claim 4, wherein said tapering is continuous along the whole distal portion.

6. The guide catheter kit in accordance with claim 4, wherein said tapering is localized in a transition portion that connects the distal portion with a proximal portion of the hollow tubular body and the lateral opening is located within the transition portion.

7. The guide catheter kit in accordance with claim 1, wherein at least the distal portion of the hollow tubular body comprises a coil support element.

8. The guide catheter kit in accordance with claim 7, wherein said coil support element is of a filiform type.

9. The guide catheter kit in accordance with claim 7, wherein said coil support element is of a ribbon-like type.

10. The guide catheter kit in accordance with claim 1, wherein the hollow tubular body has variable flexibility in an axial direction.

11. The guide catheter kit in accordance with claim 10, wherein said variable flexibility increases in a distal direction.

12. The guide catheter in kit accordance with claim 10, wherein the hollow tubular body has axially adjacent portions made from materials of differing flexibility.

13. The guide catheter kit in accordance with claim 1, wherein a proximal portion of the a hollow tubular body includes a braided layer of support.

14. The guide catheter kit in accordance with claim 1, wherein substantially all of the hollow tubular body has a flattened shape.

15. The guide catheter kit in accordance with claim 1, wherein a proximal portion of the hollow tubular body has a substantially circular cross-section.

16. The guide catheter kit in accordance with claim 1, wherein said lateral opening is positioned proximally with regard to a center of average radius of the curvature of the distal portion.

* * * * *